United States Patent
Chen et al.

(10) Patent No.: US 6,338,849 B1
(45) Date of Patent: Jan. 15, 2002

(54) PROCESS OF PREPARING IMMUNOGLOBULIN FOR INTRAVENOUS INJECTION BY VIRUSES DOUBLE-STERILIZED WITHOUT ADDING ANY PROTECTANT

(75) Inventors: Aimin Chen; Shaowen Fan; Chao Zhou, all of Chengdu (CN)

(73) Assignee: Chengdu Shuyang Pharmaceutical Factory, Chengdu (CN)

( * ) Notice: Subject to any disclaimer, the term of this patent is extended or adjusted under 35 U.S.C. 154(b) by 0 days.

(21) Appl. No.: 09/486,311

(22) PCT Filed: Jun. 21, 1999

(86) PCT No.: PCT/CN99/00081

§ 371 Date: Feb. 25, 2000

§ 102(e) Date: Feb. 25, 2000

(87) PCT Pub. No.: WO99/66955

PCT Pub. Date: Dec. 29, 1999

(30) Foreign Application Priority Data

Jun. 25, 1998 (CN) ......................................... 98112108 A

(51) Int. Cl.[7] ...................... A61K 39/395; C07K 16/06
(52) U.S. Cl. .................. 424/176.1; 530/390.1; 530/415; 530/417
(58) Field of Search ..................... 424/176.1; 530/390.1, 530/415, 417

(56) References Cited

U.S. PATENT DOCUMENTS 4,849,508 A * 7/1989 Magnin et al.
5,419,906 A * 5/1995 Mitra et al. .............. 424/176.1
6,162,904 A * 12/2000 Mamidi et al. .......... 530/390.1

OTHER PUBLICATIONS

Murphy et al., Inactivation of Hepatitis a Virus by Heat Treatment in Aqueous Solution, Journal of Medical Virology, 41(1), pp. 61–64, 1993.
Winward et al, Acute Renal Failure After Administration of Intravenous Immunoglobulin: Review of the Literature and Case Report, Pharmacotherapy, 15(6), PP. 765–722, 1995.
Hilfenhaus et al., Inactivation of Hepatitis A Virus by Pasteurization and Elimination of Picornaviruses During Manufacture of Factor VIII Concentrate, Vox Sang 67 (suppl 1), pp. 62–66, 1994.
Horowitz et al., Virucidal Short Wavelength Ultraviolet Light Treatment of Plasma and Factor VIII Concentrate: Protection of Proteins by Antioxidants, Blood, 86 (11), pp. 4331–4336, 1995.
Kempf, et al., Virus Inactivation by Pepsin Treatment at pH 4 of IgG Solutions:Factors Affecting the Rate of Virus Inactivation, Transfusion, 36(10),pp 866–872, 1996.
Yang, et al., Antibody FC Functional Activity of Intravenous Immunoglobulin . . . , Vox–Sang., 67, pp. 337–344, 1994.
Hamalainen, et al., Virus Inactivation During Intravenous Immunoglobulin Production, Vox–Sang., 63, pp. 6–11, 1992.
Li Zhenping, et al., Virus Inactivation During Preparation of Intravenous Immunoglobulin, Microorganism Immunology Progress, 24(1), pp. 40–43, 1996 (with brief English translation).
Gao Feng, et al., Introduction of Solvent/Detergent Virus Inactivation into Preparation of Intravenous Immunoglobulins, Shanghai Medicine, 17(1), pp. 18–21, 1994 (with brief English translation).
Liu Penghan, et al., A New Production Technology of Human Immunoglobulin G, Chinese Journal of Biochemical Pharmaceutics, 16(2), pp. 72–75, 1995 (with brief English translation).
Liu Penghan, et al., Studies on Preparing Technique and Quantitative Analysis of Intravenous Immunoglobulin, Pharmaceutical Biotechnology, 2(3), pp. 29–33, 1995 (with brief English translation).
Schiff RI, Virus Infection Spread by Immunoglobulin for Intravenous Injection, Foreign Medicine, 18(5), pp. 213–214, 1995 (with brief English translation).

* cited by examiner

*Primary Examiner*—David Saunders
(74) *Attorney, Agent, or Firm*—Rabin & Berdo, P.C.

(57) ABSTRACT

A process of preparing a double-sterilized immunoglobulin product for intravenous injection includes dissolving Cohn's component II in distilled ice water, and adjusting to the desired pH using acetic acid. A filter is used to remove alcohol and salt and establish a desired sodium ion concentration, and the immunoglobulin concentration is adjusted to form interim product, which is bottled. The bottle is filled with gaseous carbon dioxide to achieve a pressure of 0.7 to 200 kPa, sealed in the absence of any protectant, and sterilized. The interim product is filtered, concentrated to achieve an immunoglobulin concentration of 5% to 10%, adjusted to a desired pH, filtered to remove bacteria, and stored at room temperature for 21 days. Glucose is added in order to change the osmotic pressure equilibrium of said interim product to form final product.

2 Claims, No Drawings

PROCESS OF PREPARING IMMUNOGLOBULIN FOR INTRAVENOUS INJECTION BY VIRUSES DOUBLE-STERILIZED WITHOUT ADDING ANY PROTECTANT

This application is a 371 of PCT/CN99/00081.

FIELD OF THE INVENTION

The present invention relates to a process for preparing a biological product, particularly for preparing immunoglobulin for intravenous injection (IVIG) by using a double-sterilized method without including any protectant.

BACKGROUND OF THE INVENTION

The production of immunoglobulin started in 1949. Since the invention of IVIG in the 1960s, more than thirty (30) kinds of IVIG products, produced by 29 manufacturers in 12 countries, have appeared in the international marketplace.

Human placental blood IVIG first appeared in China in 1985, and the regulations of its manufacture and assay are recorded in "The China National Regulations of Biological Products". In 1992, pilot-plant production of lyophilized low pH IVIG was approved by the Ministry of Health of the Peoples Republic of China.

There have been many instances of epidemic type-C hepatitis caused by the repeated injection of large doses of IVIG Evidence has shown that it is difficult to ensure the safety of such injections without procedures for virus sterilization in the course of IVIG production. Since the 1990s, virus sterilization, as an essential procedure in the production of IVIG, has been regulated by many countries throughout the world.

Pasteurization was the earliest method used for virus sterilization. For example, virus sterilization may be accomplished in IVIG products by heating for 10 hours at 60° C. Methods such as low pH incubation, dry heat, irradiation, and filtration have also been developed to accomplish virus sterilization. In addition, as a result of the rapid spread of AIDS, a method using detergent to destroy the lipid-containing envelope of a virus was developed for HIV. Presently, most IVIG products are prepared using lyophilization, in which saccharose serves as a protectant and excipient.

Although the above-mentioned virus sterilization techniques are useful against the HIV, HBV, HCV, and other viruses with common pathogenic factors, differences in effectiveness among the various known methods of virus sterilization remain. Furthermore, it has been noted that a virus existing in the presence of a protectant may be better able to survive the sterilization process. According to recent literature (Ref. Murphy P. et al., J-Med-Virol, 41(1):61–64, 1993), although the presence of a protectant has some effect for keeping the natural activity of a protein, it can yield a certain protection for a virus. As a result, trace amounts of viruses may remain in the product.

In addition, organic solvents used in detergent sterilization are not completely recovered, which affects not only the purity of the product, but also can produce undesirable effects when the product is administered intravenously. For example, it has been reported in several cases that the use of saccharose as a protectant can lead to acute failure of kidney function. (Ref. Winward D B et al., Pharmacotherapy, 15(6): 765–722, 1995; Hifenhaus L.& Nowak T., Vox Sang 67 (Suppl.) 1:62–66, 1994; Horowitz B.et al., Blood, 86(11): 4331–4336, 1995).

Also, the clinical side effects of lyophilized IVIG outweigh the benefits of the liquid products because the lyophilization process causes polymerization of the IVIG molecule. Thus, the preparation of IVIG using a lyophilization process is not favorable for large-scale production.

SUMMARY OF THE INVENTION

The object of this invention is to overcome the deficiencies in the techniques for producing IVIG that use existing methods for virus sterilization. The present invention is a process for preparing a biological product, particularly for preparing immunoglobulin for intravenous injection (IVIG), by using a double-sterilized method without including any protectant. Specifically, the process incorporates a virus-sterilizing method with two different mechanisms, which serve to approach complete virus-sterilization. As a result, IVIG may be used more effectively and safely in the clinical environment.

DETAILED DESCRIPTION OF THE INVENTION

The first step for preparing immunoglobulin for intravenous injection (IVIG) according to the present invention is Pasteurization. As a raw material, Cohn's component II (F II) is dissolved in between and including 2-fold and 10-fold distilled ice water. The pH is adjusted to between and including 3.5 and 5.0 with an acetic acid solution having a concentration between and including 0.2 and 2.0 mmol/L. The solution is passed through an ultra-filter membrane having a molecular weight cut-off between and including 10 and 100 kDa, in order to remove alcohol and salt and achieve a sodium ion concentration of between and including 1 and 10 mmol/L. The IVIG concentration is adjusted to between and including 0.5% and 2% and then bottled. The bottles are filled with gaseous $CO_2$ until the internal pressure is between and including 0.7 and 200 kPa. Next, the bottles are sealed in the absence of any protectant and sterilized at 60° C.±1° C. for 10 hours.

The second step for preparing immunoglobulin for intravenous injection (IVIG) according to the present invention is incubation treatment at low pH. After Pasteurization is complete, the F II solution is cleaved and purified with an ultra-filter membrane having a molecular weight cut-off between and including 10 and 100 kDa. In the event that the IVIG solution has a purity less than 97%, the purity of the solution is increased to 97% or above using gel adsorption techniques. The IVIG solution is then concentrated to between and including 5% and 10%. The pH is adjusted to 4.1±0.3. The solution is then filtered to remove and stored at room temperature for 21 days. The osmotic is adjusted by adding between and including 5% and 10% Once quality is assured, the product may be bottled using 25 or 50 ml bottles.

In order to demonstrate the effectiveness of the present invention, virus sterilization using Pasteurization, incubation at low pH, and a combination of Pasteurization and incubation at low pH (double sterilization method) as described in the present invention is shown using the indicator viruses VSV, Polio-I, and Sindbis.

TABLE 1

Pasteurization - sterilizing effect on three kinds of viruses at 60° C.

| Sterilizing time (h) | VSV Log TCID$_{50}$/0.1 ml control sample | VSV Log TCID$_{50}$/0.1 ml Treated sample | Polio-I Log TCID$_{50}$/0.1 ml control sample | Polio-I Log TCID$_{50}$/0.1 ml treated sample | Sinbis Log PFU/ml control sample | Sinbis Log PFU/ml treated sample |
|---|---|---|---|---|---|---|
| 0 | 6 | — | 6.5 | — | $4 \times 10^6$ | — |
| 1 | 6 | 4 | 6.5 | 2 | $4 \times 10^6$ | $10^4$ |
| 4 | 6 | 3 | 6.3 | — | $4 \times 10^6$ | $<10^4$ |
| 5 | 5.8 | 2 | 6.3 | — | $4 \times 10^6$ | $<10^3$ |
| 7 | 5.8 | 1 | 6.3 | — | $4 \times 10^6$ | $<10^2$ |
| 10 | 5.8 | — | 6 | — | $4 \times 10^6$ | — |

As shown in Table 1, the sterilizing effect of Pasteurization on the Polio-I virus is remarkable, but less so for the VSV and Sindbis viruses.

TABLE 2

Low pH incubation - sterilizing effect on two kinds of viruses at pH 4.0, 23° C.

| Time (day) | VSV (Log TCID$_{50}$/0.1 ml) control sample | VSV (Log TCID$_{50}$/0.1 ml) treated sample | Sindbis (Log PFU/ml) control sample | Sindbis (Log PFU/ml) treated sample |
|---|---|---|---|---|
| 0 | 6.5 | — | $4 \times 10^6$ | — |
| 3 | 6.5 | 1 | $4 \times 10^5$ | $<10^4$ |
| 7 | 8 | — | $3.5 \times 10^6$ | $<10^3$ |
| 14 | 6 | — | $3.5 \times 10^6$ | $<10^0$ |
| 21 | 5.5 | — | $3.5 \times 10^4$ | — |

As shown in Table 2, the sterilizing effect of low pH incubation demonstrates that VSV is sensitive to an acidic environment of pH 4.0 because it was rendered inactive on the seventh day after treatment. The sterilizing effect of low pH incubation demonstrates that Sindbis is less sensitive to the same acidic environment because it was rendered inactive on the twenty-first day after treatment.

TABLE 3

Double sterilization - sterilizing effect on three kinds of viruses

| | Sterilizing time (h) | VSV Log TCID$_{50}$/0.1 ml control sample | VSV Log TCID$_{50}$/0.1 ml treated sample | Polio-I Log TCID$_{50}$/ml control sample | Polio-I Log TCID$_{50}$/ml treated sample | Sinbis Log PFU/ml control sample | Sinbis Log PFU/ml treated sample |
|---|---|---|---|---|---|---|---|
| 60° C. heating | 0 | 6 | — | 6.5 | — | $4*10^6$ | — |
| | 5 | 6 | 2 | 6.5 | — | $4*10^6$ | $10^3$ |
| | 10 | 6 | — | 6.3 | — | $4*10^6$ | — |
| Stored at pH 4.0 23° C. | 7 days | 5.5 | — | 6 | — | $3.5*10^6$ | — |
| | 14 days | 5.5 | — | 6 | — | $3.5*10^6$ | — |
| | 21 days | 5 | — | 5.5 | — | $3.5*10^6$ | — |

As shown in Table 3, the effect of double sterilization demonstrates that all three indicator viruses have been inactivated after 10 hours of Pasteurization.

In order to further demonstrate the effectiveness of the present invention, the National Institute for Control of Pharmaceutical and Biological Products and AIDS Detection and Confirmation Laboratory of the People's Liberation Army (PLA) obtained the following results after conducting a separate series of tests. These are shown in Table 4 and Table 5.

TABLE 4

Pasteurization - sterilizing effect on four kinds of viruses at 60° C.

| Time (h) | VSV Log TCID$_{50}$/0.1 ml | | Polio-I Log TCID$_{50}$/0.1 ml | | HIV Log TCID$_{50}$/0.1 ml | | Sindbis Log PFU/ml | |
|---|---|---|---|---|---|---|---|---|
| | control sample | treated sample | control sample | treated sample | control sample | treated sample | control sample | treated sample |
| 0 | 7.00 | 5.00 | 6.00 | 3.13 | 6.00 | 5.77 | — | 6.63 |
| 0.5 | ≦−0.50 | ≦0.50 | ≦−0.50 | ≦0.50 | — | — | — | ND |
| 1 | ≦−0.50 | ≦0.50 | ≦−0.50 | ≦0.50 | — | — | — | ND |
| 4 | ≦−0.50 | ≦0.50 | ≦−0.50 | ≦0.50 | — | — | — | ND |
| 6 | ≦−0.50 | ≦0.50 | ≦−0.50 | ≦0.50 | — | — | — | — |
| 10 | ≦−0.50 | ≦0.50 | ≦−0.50 | ≦0.50 | — | — | — | ND |
| | | | | | ≦5.80 | <2.00 | — | — |

In this experiment, samples were treated by Pasteurization, which was accomplished by heating the samples at 60° C. for 10 hours. As shown, there was substantial sterilization for the indicator viruses VSV, HIV, Sindbis, and Polio-I. After heating for 30 minutes, the virus titers were decreased below the detection limit. The viruses that experienced decreases were VSV: ≧4.50–4.63 log TCID$_{50}$/0.1 ml, Polio-I: ≧2.63–3.63 log TCID$_{50}$/0.1 ml, HIV: ≧3.77–4.17 log TCID$_{50}$/0.1 ml, and Sindbis: ≧6.32–6.41 log PFU/ml, respectively. For the samples in which heating lasted 6 hours and 10 hours, three generations of blind passage were negative. The virus minimal detection limits were: ≦0.50 Log TCID$_{50}$/0.1 ml, titer of Sindbis basal virus: 7.70 log PFU/ml. An "ND" indicates that no virus was detected.

TABLE 5

Low pH incubation - sterilizing effect on three kinds of viruses at room temperature

| Time (days) | VSV Log TCID$_{50}$/ 0.1 ml | | HIV* Log TCID$_{50}$/ 0.1 ml | | Sindbis Log PFU/ml | |
|---|---|---|---|---|---|---|
| | Acid | Neutral | Acid | Neutral | Acid | Neutral |
| 0 | 3.88 | 6.38 | 5.77 | 6.00 | 3.75 | 7.34 |
| 3 | 3.13 | 6.13 | — | — | ND | 7.09 |
| 7 | 1.75 | 5.88 | <2.00 | 5.80 | ND | 7.09 |
| 14 | ≦0.50 | 5.18 | — | — | ND | 6.60 |
| 21 | ≦0.50 | 4.88 | — | — | ND | 6.23 |

In this experiment, samples were incubated at a pH of 4.0±0.2 and a temperature of between 22 and 24C. for 21 days. The viruses that experienced decreases were VSV: ≧5.88–6.63 log TCD$_{50}$/0.1 ml, HIV: ≧3.77–4.17 log TCD$_{50}$/0.1 ml, and Sindbis: ≧7.33–7.74 log PFU/ml. Three generations of blind passage were negative. The virus minimal detection limits were: ≦0.50 Log TCID$_{50}$/0.1 ml, titer of Sindbis basal virus: 8.35 log PFU/ml. An "ND" indicates that no virus was detected. An "*" indicates that a sample after Pasteurization was used.

In summary, the following conclusions may be drawn from the experiments described above:
1. Pasteurization at 60° C. for 10 hours is capable of sterilizing four kinds of indicator virus. This is particularly effective for VSV and Polio-I viruses.
2. Low pH incubation provides a strong sterilizing effect on VSV, HIV, and Sindbis viruses, which were completely inactive in 7 days.
3. Double-sterilization, which includes Pasteurization for 10 hours followed by room temperature incubation at pH 4.0 for 21 days, demonstrated that all indicator viruses are inactivated more thoroughly.

As compared to existing techniques, the advantages, as described herein, for preparing immunoglobulin for intravenous injection (IVIG) according to the present invention by using a double-sterilized method without including any protectant are as follows:
1. The process described by the present invention does not incorporate any protectant constituent. As a result, the process effectively inactivates viruses while maintaining the integrity of the IVIG molecule and ensuring the natural biological activity, purity, and safety of the product.
2. The process described by the present invention allows for the liquidus preparation of IVIG, rather than a lyophilized powder process. As a result, the process shortens production time, reduces energy consumption, and favors large-scale production while maintaining a stable and reliable product.
3. The process of the present invention incorporates glucose in the product, which adjusts the osmotic pressure equilibrium of the solution. As a result, this offers certain patients relief from undesirable effects after IVIG is administered.

EXAMPLES

Example 1

The first step for preparing human blood IVIG using the double-sterilization without including any protectant method of the present invention is Pasteurization. A 16.5 kg F II precipitate is dissolved in 165 liters of distilled water at 0° C. The pH is adjusted to 3.5 using a 1 mmol/liter acetic acid solution. The solution is passed through an ultra-filter membrane having a molecular weight cut-off of 100 kDa, in order to remove alcohol and salt and achieve a sodium ion concentration of 1.2 mmol/liter. The immunoglobulin concentration is adjusted to 1.5% and the solution is bottled and sealed. The internal pressure is adjusted to 100 kPa by charging with carbon dioxide. The solution is then sterilized at 60° C.±1° C. for 10 hours.

The second step is an incubation treatment at low pH. After Pasteurization, the F II solution is cleaved and purified with an ultra-filter membrane having a molecular weight cut-off of 100 kDa. In the event that the immunoglobulin solution has a purity of less than 97%, the purity of the solution may be increased to greater than or equal to 98% using DEAE-Sephadex A-50 gel adsorption. The immunoglobulin is concentrated to 5% and the pH is adjusted to 4.1. The solution is then filtered in order to remove bacteria. The solution is then stored for 21 days after which 5% glucose is added. The product is then tested for its physical and chemical properties including pyrogen and sterility tests according to the regulations governing human blood immunoglobulin. If the product passes the tests, it is filtered to remove bacteria and bottled in 25 or 50 ml bottles.

Example 2

The first step for preparing human blood IVIG using the double-sterilization without including any protectant method of the present invention is Pasteurization. A 15 kg F II precipitate is dissolved in 150 liters of distilled water at 0° C. The pH is adjusted to 5.0 using a 0.2 mmol/liter acetic acid solution. The solution is passed through an ultra-filter membrane having a molecular weight cut-off of 10 kDa, in order to remove alcohol and salt and achieve a sodium ion concentration of 10 mmol/liter. The immunoglobulin concentration is adjusted to 2% and the solution is bottled and sealed. The internal pressure is adjusted to 0.7 kPa by charging with carbon dioxide. The solution is then sterilized at 60° C.±1° C. for 10 hours.

The second step is an incubation treatment at low pH. After Pasteurization, the F II solution is cleaved and purified with an ultra-filter membrane having a molecular weight cut-off of 10 kDa. In the event that the immunoglobulin solution has a purity less than 97%, the purity of the solution may be increased to greater than or equal to 98% using DEAE-Sephadex A-50 gel adsorption. The immunoglobulin is concentrated to 8% and the pH is adjusted to 4.1. The solution is then filtered in order to remove bacteria. The solution is then stored for 21 days after which 10% glucose is added. The product is then tested for its physical and chemical properties including pyrogen and sterility tests according to the regulations governing human blood immunoglobulin. If the product passes the tests, it is filtered to remove bacteria and bottled in 25 or 50 ml bottles.

Example 3

The first step for preparing human blood IVIG using the double-sterilization without including any protectant method of the present invention is Pasteurization. A 16.5 kg F II precipitate is dissolved in 165 liters of distilled water at 0° C. The pH is adjusted to 4.2 using a 2.0 mmol/liter acetic acid solution. The solution is passed through an ultra-filter membrane having a molecular weight cut-off of 50 kDa, in order to remove alcohol and salt and achieve a sodium ion concentration of 5 mmol/liter. The immunoglobulin concentration is adjusted to 0.5% and the solution is bottled and sealed. The internal pressure is adjusted to 200 kPa by charging with carbon dioxide. The solution is then sterilized at 60° C.±1° C. for 10 hours.

The second step is an incubation treatment at low pH. After Pasteurization, the F II solution is cleaved and purified with an ultra-filter membrane having a molecular weight cut-off of 50 kDa. In the event that the immunoglobulin solution has a purity less than 97%, the purity of the solution may be increased to greater than or equal to 98% using DEAE-Sephadex A-50 gel adsorption. The immunoglobulin is concentrated to 10% and the pH is adjusted to 4.1. The solution is then filtered in order to remove bacteria. The solution is then stored for 21 days after which 8% glucose is added. The product is then tested for its physical and chemical properties including pyrogen and sterility tests according to the regulations governing human blood immunoglobulin. If the product passes the tests, it is filtered to remove bacteria and bottled in 25 or 50 ml bottles.

What is claimed is:

1. A process of preparing a double-sterilized immunoglobulin without protectant product for intravenous injection comprising:

dissolving Cohn's component II in between and including 2-fold and 10-fold distilled ice water;

adjusting to a pH of between and including 3.5 and 5.0 with between and including 0.2 and 2.0 mmol/liter acetic acid;

filtering with an ultra-filter membrane having a molecular weight cut-off of between and including 10 kDa and 100 kDa to remove alcohol and salt and establish a sodium ion concentration of between and including 1 and 10 mmol/liter;

adjusting the immunoglobulin concentration to between and including 0.5% and 2% to form interim product;

adding said interim product to a bottle;

filling said bottle with gaseous carbon dioxide to achieve a pressure of between and including 0.7 and 200 kPa;

sealing said bottle in the absence of any protectant;

sterilizing said bottle containing said interim product at a temperature between and including 59° C. and 61° C. for 10 hours;

filtering said interim product with an ultra-filter membrane having a molecular weight cut-off of between and including 10 kDa and 100 kDa;

concentrating said interim product to achieve an immunoglobulin concentration of between and including 5% and 10%;

adjusting to a pH of between and including 3.8 and 4.4;

filtering said interim product to remove bacteria;

storing said interim product at room temperature for 21 days; and adding between and including 5% and 10% glucose in order to change the osmotic pressure equilibrium of said interim product to form final product.

2. The process of claim 1, comprising an additional step after filtering said interim product with an ultra-filter membrane having a molecular weight cut-off of between and including 10 kDa and 100 kDa of applying said interim product to a gel adsorption medium in order to improve purity.

* * * * *